United States Patent [19]
Edenbaum

[11] Patent Number: 5,476,440
[45] Date of Patent: Dec. 19, 1995

[54] ORTHOPEDIC BANDAGE WITH LUBRICIOUS CORE

[75] Inventor: Martin Edenbaum, Princeton Junction, N.J.

[73] Assignee: Carapace, Inc., Broken Arrow, Okla.

[21] Appl. No.: 277,557

[22] Filed: Jul. 19, 1994

[51] Int. Cl.⁶ ............................................. A61L 15/08
[52] U.S. Cl. ....................................... 602/8; 602/6
[58] Field of Search ............................. 602/8, 12, 17, 602/18, 19, 20, 23, 304, 307; 128/90; 428/143, 253

[56] References Cited

U.S. PATENT DOCUMENTS

| | | | |
|---|---|---|---|
| 2,964,174 | 12/1960 | Litchfield et al. | 206/59 |
| 3,062,370 | 11/1962 | Morin | 206/63.2 |
| 3,152,692 | 10/1964 | Johnston | 206/59 |
| 3,630,194 | 12/1971 | Boardman | 128/90 |
| 4,020,832 | 5/1977 | Kirkpatrick et al. | 128/90 |
| 4,131,114 | 12/1978 | Kirkpatrick et al. | 128/90 |
| 4,153,052 | 5/1979 | Tsuk | 128/90 |
| 4,344,423 | 8/1982 | Evans et al. | 128/90 |
| 4,376,438 | 3/1983 | Straube et al. | 128/90 |
| 4,411,262 | 10/1983 | von Bonin et al. | 128/90 |
| 4,433,680 | 2/1984 | Yoon | 128/90 |
| 4,498,467 | 2/1985 | Kirkpatrick et al. | 128/90 |
| 4,502,479 | 3/1985 | Garwood et al. | 128/90 |
| 4,667,661 | 5/1987 | Scholz et al. | 128/90 |
| 4,774,937 | 10/1988 | Scholz et al. | 128/90 |
| 4,960,116 | 10/1990 | Milner | 128/90 |
| 5,061,555 | 10/1991 | Edenbaum et al. | 428/253 |
| 5,250,344 | 10/1993 | Willliamson et al. | 428/143 |

FOREIGN PATENT DOCUMENTS

| | | |
|---|---|---|
| 0522826 | 1/1993 | European Pat. Off. . |
| 0522824 | 1/1993 | European Pat. Off. . |
| 0522825 | 1/1993 | European Pat. Off. . |
| 522825A1 | 1/1993 | European Pat. Off. ........ A61F 13/04 |

*Primary Examiner*—Corrine M. Maglione
*Assistant Examiner*—Michael L. Arness
*Attorney, Agent, or Firm*—Panitch Schwarze Jacobs & Nadel

[57] ABSTRACT

The bandage has a substrate, a tacky liquid-curable prepolymer resin in contact with the substrate and a permeable core on which said substrate is wrapped for storage. The core of the bandage has a lubricant adapted to be released from the core such that the lubricant renders the surface portion of the substrate substantially non-tacky to facilitate molding, laminating and smoothing of a cast to be formed from the bandage. The cores have a liquid-permeable base and a lubricant in accordance with the lubricant provided to the core of the bandage. The method includes unwinding the bandage from the core, applying the bandage to a limb to form a cast, contacting the core with liquid, applying force to the core to release lubricant from the core onto the applier's hands and molding, laminating and smoothing a surface portion of the cast rendered substantially non-tacky by the lubricant on the applier's hands.

28 Claims, 2 Drawing Sheets

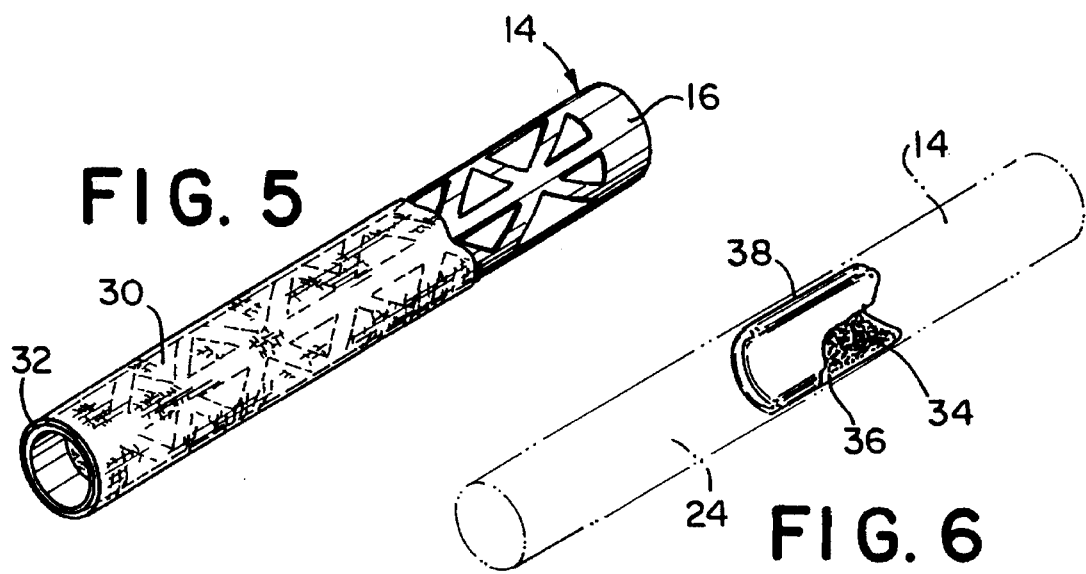
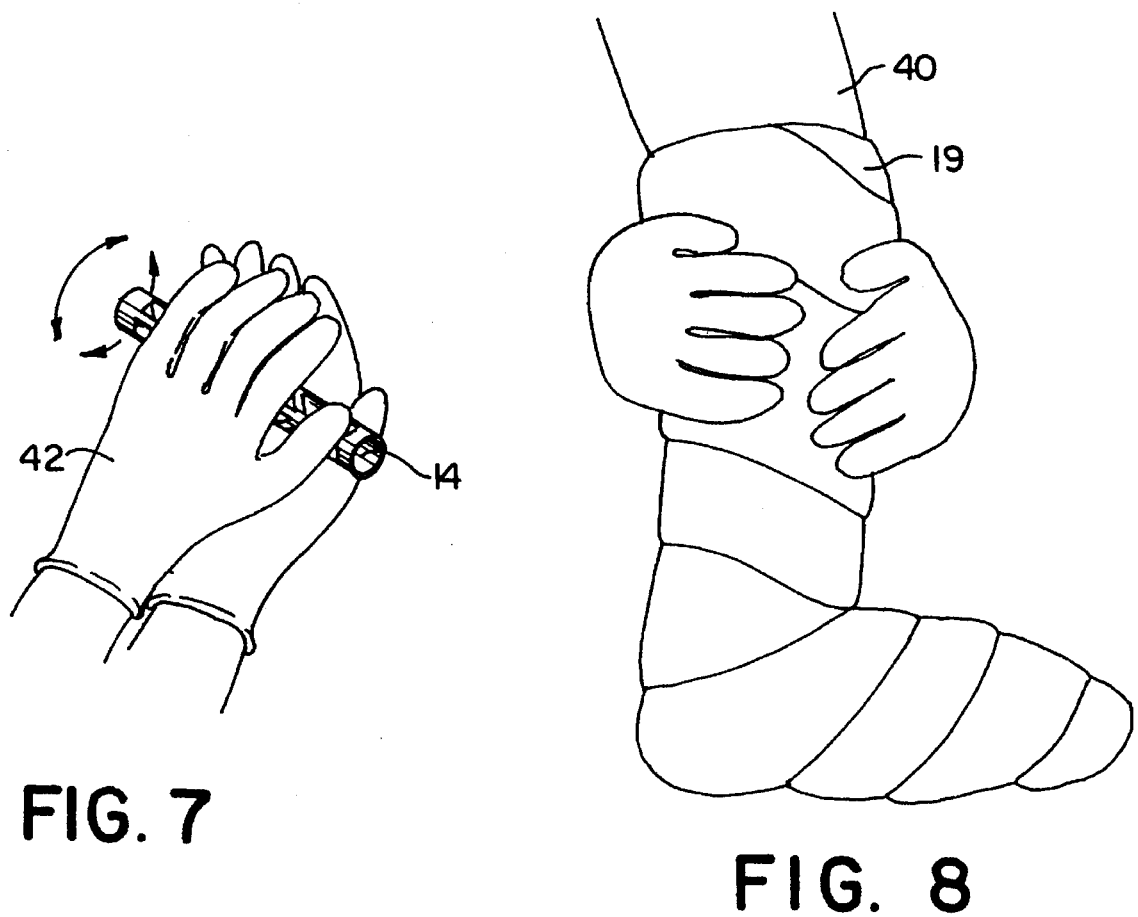

5,476,440

ORTHOPEDIC BANDAGE WITH LUBRICIOUS CORE

FIELD OF THE INVENTION

The present invention relates to an orthopedic bandage material having a lubricant and a core upon which a substrate is wrapped for storage, and a method of making an orthopedic cast for a limb.

BACKGROUND OF THE INVENTION

Historically, orthopedic surgeons and other specialists have worked with Plaster of Paris in the preparation of surgical casts. The problems associated with Plaster of Paris regarding its weight, susceptibility to water damage and insufficient x-ray opacity are well known in the art. These problems led to the development, and to a large extent, the replacement of Plaster of Paris with orthopedic bandages which utilize cast forming compositions and mixtures using water soluble vinyl monomers such as diacetone acrylamide (DAA) and N-isopropylacrylamide (N-IPA) wherein the monomers are polymerizable in the presence of water by means of an amine catalyst or a redox catalyst system that comprises an oxidation component and a reducing agent. Such orthopedic bandages are described, for example, in U.S. Pat. No. 3,630,194.

Also available as substitutes for Plaster of Paris are polyurethanes and cyanoacrylate esters. In addition, isocyanate prepolymer impregnated resins are available including those described in U.S. Pat. Nos. 4,411,262, 4,502,479 and 4,131,114. The bandages are hardened in a manner similar to the Plaster of Paris bandages by dipping the bandage into tap water which is then formed about the portion of the body to be immobilized or supported. Other prior art orthopedic bandages are found, for example, in U.S. Pat. Nos. 4,411, 262, 4,376,438, 4,344,423, 4,502,479 and 4,433,680.

Typically, a prepolymer containing bandage is soaked in water prior to application to the body member. The wet bandage is then applied to the body member. After the bandage is applied, the cast is smoothed and molded with the applier's gloved hand and held at certain points until it hardens. Since the resins in the bandage are quite tacky until they cure completely, the protective gloves worn by the cast applier tend to stick to the bandage. This is disadvantageous as it can lead to delamination of the cast as layers of the tape pull apart from each other and the cast cannot be molded.

To alleviate this problem of "tackiness" in curable resin-coated bandages, Scholz et al. proposed in U.S. Pat. Nos. 4,667,661 and 4,773,937 that bandage sheets be pretreated by coating the surface of the bandage sheets with certain lubricants to reduce the kinetic coefficient of friction of such sheets to less than about 1.2. As noted in the Scholz et al. patents, the bandages treated with the described lubricants become very slippery, and molding of the cast becomes easier due to the reduced tackiness of the resin. The lubricant selected is from a variety of materials such as hydrophilic groups which are bonded to the curable resin or an additive which is incompatible with the curable resin, such as a surfactant, a polymer comprised of a plurality of hydrophilic groups or a polysiloxane.

While the Scholz et al. pre-coated sheets solve some of the tackiness problem, these sheets tend to be very slippery immediately after removal from the water bath used to activate the resin. The slipperiness makes it difficult for the applier of the cast to hold the tape securely and manipulate it into the form of a well fitting cast. The interlaminar strength of the final cast is also compromised due to the interference of the lubricant with the adhesive bonds which must form between the bandage layers.

A further attempt to solve the tackiness problem is included in U.S. Pat. No. 5,250,344 of Williamson et al. which proposes including microgranules of encapsulated lubricant in sizes ranging from 100 to 300 microns on only a portion of one side of a bandage substrate. The substrate is wound around a core for storage with the microgranules positioned such that they are on the end of the bandage closest to the core. The bandage substrate, including the microgranules, is then applied to the body member such that the end of the bandage substrate having the microgranules is applied as the outer portion of the cast. The applier of the cast then squeezes the outer portion of the bandage substrate, now formed into a cast, thereby bursting the microgranules and releasing lubricant over the entire surface of the cast. The lubricant released is then used to smooth the cast.

While Williamson et al. improve upon the Scholz et al. interlayer delamination problem, the applier of a cast using the Williamson et al. lubricated bandage still lacks adequate control over the quantity of the lubricant required in an individual case and the timing of the lubricant's release. In an optimal situation, the amount of lubricant available or the level of tackiness required at any given time and at different areas of the cast should be completely controlled by the applier, while he or she is molding the cast.

European Patent Applications Nos. 0 522 826 A1, 0 522 825 A1 and 0 522 824 A1 of Johnson & Johnson also attempted to solve the tackiness problem without affecting interlayer lamination of the cast by providing a glove having a dry, water-activatable lubricant material on the outside of the glove. While a lubricated glove may be helpful toward solving the tackiness and delamination problems, like Williamson et al., the applier still cannot adequately control the quantity of lubricant available during application. In addition, the lubricated gloves are not available in all necessary sizes and materials preferred by different surgeons and technicians.

One further solution is to provide lubricant separately in the form of a separate bar. An example of such a bar is the Poly Bithane™ No Tac bar of Carapace, Incorporated of Broken Arrow, Okla. While this helps to solve the lubricant control problem, it introduces a separate item into the cast bandage packaging, further adding to the costs of packaging and manufacture as well as necessitating disposal of the unused portion of the bar as an extra waste item.

Therefore, a need in the art still exists for an efficient, economical device and a method for applying a water-curable resin casting bandage which allows the applier to apply a cast without experiencing excessive tackiness while molding, smoothing and laminating the cast and which provides lubrication without unwanted delamination of the cast layers while the cast is hardening. Such a device and method should give the applier adequate control over the quantity and area of application of lubricant without needlessly limiting the applier's use of existing medical supplies, such as gloves, and without introducing extraneous items to the packaging of the casting bandage.

SUMMARY OF THE INVENTION

The present invention includes an orthopedic bandage which comprises a substrate, a tacky resin in contact with the substrate and a permeable core on which the substrate is wrapped for storage. The core comprises a lubricant adapted to be released from the core such that the lubricant renders a surface portion of the substrate substantially non-tacky, thus facilitating molding, laminating and smoothing of the cast to be formed from the bandage.

The invention also includes a core upon which a casting bandage may be wrapped for storage. The core comprises a liquid-permeable base and a lubricant adapted to be released from the base. The lubricant renders a surface portion of a substrate to be used as an orthopedic casting bandage substantially non-tacky thereby facilitating the molding, laminating and smoothing of the cast.

In addition, the present invention includes a method for applying an orthopedic cast on a limb. The method comprises the steps of providing a tacky orthopedic casting bandage on a core which comprises a lubricant. The bandage is unwound from the core and applied to the limb to form a cast. Force is applied to the exterior surface of the core to release the lubricant. The lubricant is applied to a tacky surface of the cast. A surface portion of the cast which is rendered substantially non-tacky by application of the lubricant is then molded, laminated and smoothed.

BRIEF DESCRIPTION OF THE DRAWINGS

The foregoing summary, as well as the following detailed description of preferred embodiments of the invention, will be better understood when read in conjunction with the appended drawings. In the drawings, like numerals are used to indicate like elements throughout. For the purpose of illustrating the invention, there are shown in the drawings embodiments which are presently preferred. It should be understood, however, that the invention is not limited to the precise arrangements and instrumentalities shown. In the drawings:

FIG. 5 is a perspective view of an embodiment of a core in accordance with the present invention in which a water-permeable fabric sheet is wrapped around the core such that the surface of the sheet facing the core is coated with lubricant.

FIG. 6 is a perspective view of an embodiment of a core in accordance with the present invention in which lubricant is provided in the form of a powder enclosed within a water-permeable fabric casing.

FIG. 7 is a perspective view showing wet gloved hands applying manual force to a core of the present invention to release lubricant from the core in accordance with the method of the present invention.

FIG. 8 is a schematic view of a cast applied to the limb of a patient being molded, smoothed and laminated by gloved hands which have been lubricated as shown in FIG. 7.

DETAILED DESCRIPTION OF PREFERRED EMBODIMENTS

Figure 1:
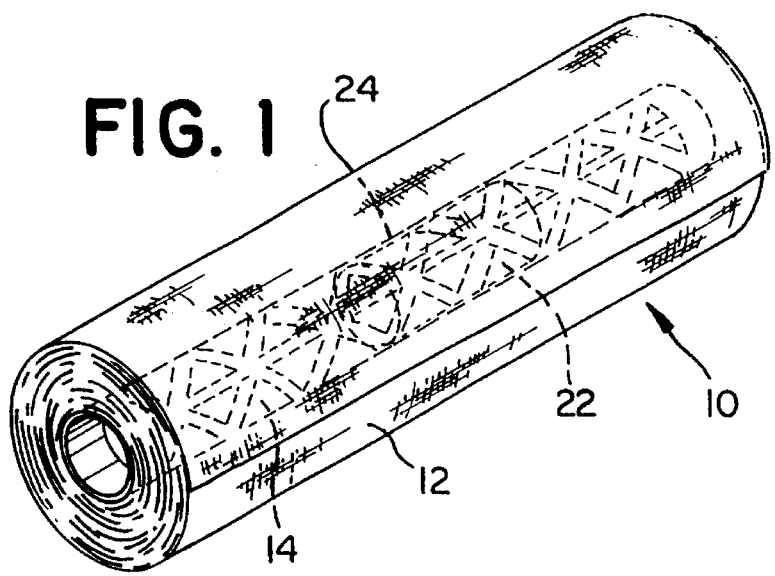
FIG. 1 is a perspective view of an orthopedic casting bandage in accordance with one embodiment of the present invention.

Certain terminology is used in the following description for convenience only and is not limiting. The words "right," "left," "lower" and "upper" designate directions in the drawings to which reference is made. The terminology includes the words above specifically mentioned, derivatives thereof, and words of similar import.

Figure 3:
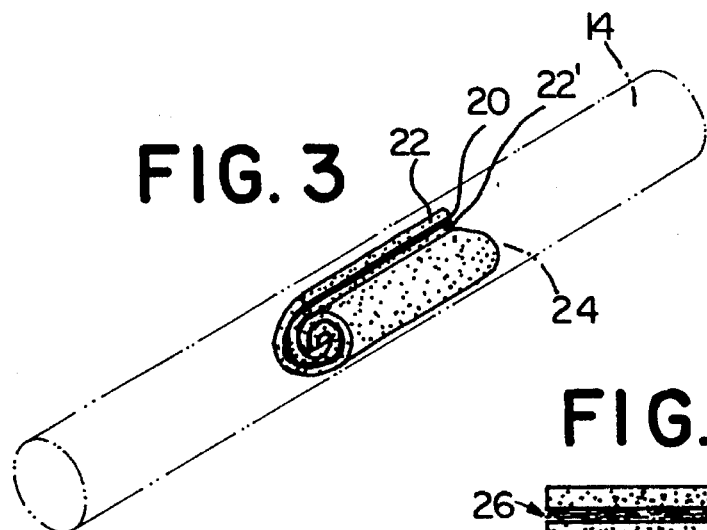
FIG. 3 is a perspective view of an embodiment of a core in accordance with the present invention in which two foam layers coated with lubricant are folded and inserted in the core.
Figure 4:
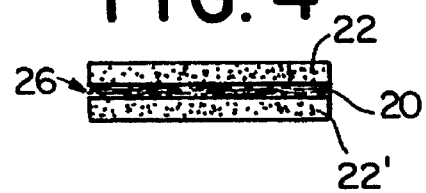
FIG. 4 is a side elevational view of a layered foam structure for use in the core as shown in FIG. 3.

Referring now to the drawings in detail, there are shown in FIGS. 1, 3 and 4, embodiments of an orthopedic bandage and a core upon which a casting bandage may be wrapped for storage in accordance with the present invention.

As shown in FIG. 1, in the orthopedic bandage of the present invention, generally designated as 10, a substrate, generally designated as 12 is provided around a core 14. The substrate 12 bandage fabric may be any suitable fabric useful for resin-impregnated casting bandages. Preferably the substrate 12 is made of a fiberglass warp-knit fabric, wherein the weft or fill yarns of the fabric preferably are made of fiberglass, thermoplastic yarn, natural fiber, thermoplastic/natural fiber blends or combinations thereof. More preferably, the substrate 12 is made of a fiberglass warp and a combination fiberglass and thermoplastic yarn weft. The most preferred fabric is described in co-pending application Ser. No. 08/098,535 assigned to Carapace, Incorporated of Broken Arrow, Okla. Other suitable fabrics which may be used for the substrate 12 may be found, for example, in U.S. Pat. Nos. 4,667,661 and 4,411,262.

The substrate 12 is in contact with a tacky resin. The resin is preferably a water- or other liquid-curable, prepolymer resin useful in the art of casting bandages. Preferably, the resin is water-curable, and is preferably the reaction product of an isocyanate and a propylene glycol. More specifically, the resin is preferably a polyisocyanate prepolymer derived from polyisocyanate, preferably aromatic, and a reactive hydrogen compound or oligomer. The preferred prepolymer composition comprises modified diphenylmethane diisocyanate, polypropylene glycol, benzoyl chloride stabilizer and dimorpholinodiethyl-ether catalyst. The preferred isocyanate to diol ratio is about 4 to 1 (NCO/OH= 4:1). In addition, the resin may be impregnated in or coated upon the substrate 12. Preferably, the resin is impregnated within the substrate 12.

It will be understood by one skilled in the art that other suitable tacky resins which are useful in casting bandages may be used in contact with the present substrate 12 without departing from the scope of the invention.

Figure 2:
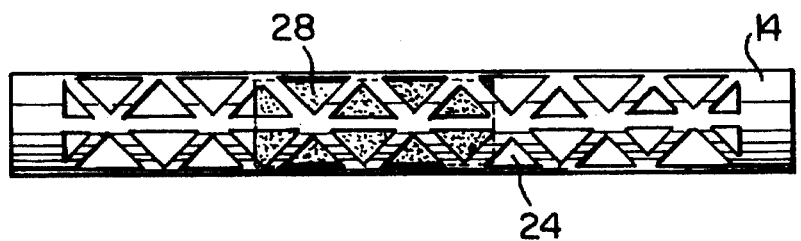
FIG. 2 is a longitudinal side view of an embodiment of a core in accordance with the present invention in which the lubricant is provided in the form of a pellet.

The substrate 12 in contact with the resin is wound around the core 14. The core 14 is liquid-permeable such that water or other liquid-activating substance may freely flow through the core from the exterior surface 16 of the core 14 to the interior surface 18 of the core. A preferred core 14 configuration is shown in FIGS. 1, 2 and 5. It will be understood by those skilled in the art, however, that any liquid permeable core 14 configuration may be used in the present invention which allows free flow of a resin-activating liquid through the core 14.

The core 14 in accordance with the present invention includes a base 15 and a water- or other liquid-activatable lubricant, which may be included in the core 14 in various ways as discussed below.

With respect to the orthopedic bandage 10 and the core 14 of the present invention, the lubricant is adapted to be released from the core 14 such that a surface portion of substrate 12 may be rendered substantially non-tacky. As such, molding, laminating and smoothing of the cast 19 is facilitated by the release of the lubricant. Preferably, the lubricant is released from the core 14 after the substrate 12 has been applied to a patient to form a cast 19 as shown in FIG. 8.

The lubricant may be any suitable, preferably water-activatable, lubricous substance suitable for use in smoothing a cast 19 which is capable of reducing friction or reducing interfacial tension between the applier's hands and the casting bandage substrate 12 and between layers of the substrate 12 when applied as a cast 19. The lubricant may be solid, liquid or semi-solid and is preferably non-toxic. The lubricant may include emulsifiers, surfactants or other lubricants deemed suitable for use by those of ordinary skill in the art depending upon the embodiment of the orthopedic bandage 10 and core 14 as described further below. The lubricant is preferably a hydrophilic, water-activatable bisurethane. However, it should be understood by those of ordinary skill in the art that other lubricants may be core-incorporated in accordance with the present invention without departing from the scope of the invention.

The preferred bisurethanes of the present invention are preferably the compounds described in detail in U.S. Pat. No. 5,061,555 assigned to Carapace Incorporated, Broken Arrow, Okla. which is incorporated herein by reference.

The base 15 is preferably made of a plastic or resin material which is sufficiently rigid to adequately support the substrate 12 wrapped around the core 14 for storage. The base 15 is preferably made of any thermosetting or thermoplastic polymeric material which may be molded to the desired configuration. Preferably, the base 15 is made of polyolefin homopolymers or copolymers of, for example, polypropylene and polyethylene. More preferably, the base 15 is made of a polypropylene homopolymer.

Preferably, as shown in FIGS. 3 and 4, lubricant 20 is provided to the preferred core 14 of the present invention by coating the lubricant 20 on at least one layer 22 of liquid-permeable foam material. Any liquid-permeable foam material may be used in the present invention. Preferably the foam is made of a polyurethane, and more preferably, an open-cell polyurethane. The foam layer 22 having a lubricant coating 20 is located within an interior portion 24 of the base 15 of the core 14. When the base 15 is contacted with water or other activating liquid, the applier of the cast then applies force, such as rubbing, squeezing or similar manual force, to the exterior surface 16 of the core 14 which thereby releases lubricant from the layer 22.

Preferably, there are at least two layers 22, 22' arranged in facing engagement with each other forming a layered foam structure 26 as shown in FIG. 4 to be placed within the core 14. The coating of lubricant 20 is located between the two foam layers 22, 22'. More preferably, the foam layer 22 or foam structure 26 is folded within the interior portion 24 of the base 15 as shown in FIG. 3.

In an alternative embodiment of the core 14 of the present invention, as shown in FIG. 2, the lubricant contained within the interior portion 24 of the base 15 is in the form of a solid lubricant pellet 28. The pellet 28 is preferably formed primarily of lubricant material, however, other fillers and additives such as gypsum, talc, calcium carbonate, calcium sulfate and other similar materials may be added to the lubricant pellet 28. Preferably, the lubricant pellet 28 is a solid, bisurethane pellet 28. When the core 14 has been contacted with water or other activating liquid such that the pellet 28 is wet, and force is applied to the exterior surface 16 of the core 14, the lubricant is released from the pellet 28.

In a further alternative embodiment of the core 14, a preferably non-woven, liquid-permeable fabric sheet or sheath 30 is wrapped at least partially, preferably completely, around the exterior surface 16 of the base 15 of the core 14. The surface 32 of the sheet 30 which faces the exterior surface 16 of the core 14 is coated with lubricant. When the core 14 is contacted with water or other liquid and the force is applied to the exterior surface 16 of the core 14, the lubricant is released from the fabric sheet 30.

Preferably the sheet 30 is made of a porous, non-woven fabric containing, for example, spun polypropylene, polyester, polyethylene, bonded non-woven cellulose and similar materials. Commercially available porous, non-woven fabrics suitable for the present invention include, for example, Sontara® available from Kimberly Clark Corporation and Paramol® available from Lohmann GmbH & Co. KG, in Neuwied, Federal Republic of Germany. However, it is understood by those of ordinary skill in the art, that any suitable, porous fabric may be used for the sheet 30 which can sustain a coating of lubricant and which allows water or other liquid to pass through the sheet 30 and permeate the base 15. Preferably, the lubricant used for coating the sheet 30 is bisurethane.

The core 14 of the present invention, as shown in FIGS. 2 and 5, may also be made in accordance with the present invention without the use of a pellet 28 or sheet 30, by alternatively incorporating lubricant material at least partially into polymeric composition forming the base 15 of the core 14 itself. In such case, the polymer or polymers forming the base 15 are blended with the selected lubricant chosen to form a polymeric composition which is then molded into the base 15. When the lubricant material is blended into the polymeric composition of the base 15, the polymer or polymers selected are preferably compatible with the lubricant material. Suitable polymers to be used for blending with bisurethane as the core 14 include, for example, polyolefins such as polypropylene, polyethylene and copolymers thereof. However, other similar thermoplastic or thermosetting polymers may be used to form the polymeric composition incorporating the lubricant without departing from the scope of the present invention.

Other polymers, fillers, compatibilizers and additives, such as plasticizers may be added, if necessary, to improve molding of the core 14 and to compatibilize the polymer or polymers selected with each other and with the lubricant. The choice of any additives, fillers or compatibilizers is dependent upon the base polymer or polymers chosen as well as the lubricant to be incorporated.

Preferably, the base 15 is made of polyolefin, more preferably, the base 15 is made of polypropylene blended with waner-activatable bisurethane lubricant and molded by a method such as, for example, injection molding. When the base 15 material is contacted with water or other activating liquid and the force is applied to the exterior surface 16 of the core 14, the base 15 material releases the incorporated lubricant to the applier's gloved hands.

A further alternative embodiment of the core 14 includes a powdered lubricant 34 enclosed within the interior portion 36 of a liquid-permeable fabric casing or packet 38. The packet 38 is preferably formed of a non-woven, liquid-permeable fabric such as, for example, polypropylene, polyester, polyethylene, non-woven bonded cellulose and similar materials. Commercially available non-woven fabrics suitable for the packet 38 include, for example, Paramol® and Sontara® as described above. The powdered lubricant 34 is preferably water-activatable bisurethane. The packet 38 is contained within an interior portion 24 of the base 15 of the core 14.

When the core 14 is contacted with water or other activating liquid, the liquid permeates the fabric of the packet 38 and contacts and activates the powdered lubricant 34. When force is applied to the exterior surface 16 of the base 15, the lubricant is released through the packet 38 and base 15.

The method of the present invention is a method for applying an orthopedic cast 19 for a limb 40. In the method, a tacky orthopedic casting bandage substrate 12, such as that shown in FIG. 1, is provided on a core 14 which comprises a lubricant. The bandage substrate 12 is unwound from the core 14. The bandage 12 is applied to the limb 40 to form a cast 19.

After the cast 19 is formed, the core 14 is preferably contacted with an activating liquid, preferably water, such that the liquid-activatable lubricant is more easily released from the core 14. Force is applied to the exterior surface 16 of the base 15 of the core 14 to release the lubricant. Preferably, the force is applied by rubbing the core 14 between the preferably gloved hands 42 of the applier as shown in FIG. 7 or by squeezing the core 14 between the applier's hands 42. The lubricant is released in the desired quantity to the gloved hands 42 and is then applied with preferably gloved hands 42 to the tacky surface of the cast 19. The lubricant is then used to facilitate molding, laminating and smoothing a portion of the surface of the cast 19 which is rendered substantially non-tacky by application of the lubricant as shown in FIG. 8.

The applier has the ability to direct the appropriate quantity of lubricant on exactly the areas of the cast 19 which require the lubricant while he or she is molding the cast 19. As the lubricant is only applied to the exterior of the cast 19, the interlayer lamination is not affected.

The applier may also re-apply force to the exterior surface 16 of the core 14 to release further lubricant as required in molding, laminating and smoothing the cast 19.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An orthopedic bandage for forming a cast, comprising:
   (a) a substrate;
   (b) a tacky resin in contact with the substrate; and
   (c) a liquid-permeable core on which said substrate is wrapped for storage, said core comprising a lubricant adapted to be released from the core such that the lubricant renders a surface portion of the substrate substantially non-tacky, thus facilitating molding, laminating and smoothing of the cast to be formed from the bandage.

2. The bandage according to claim 1, wherein the lubricant is a hydrophilic bisurethane.

3. The bandage according to claim 1, wherein the tacky resin is liquid-activatable and is tacky after liquid activation.

4. The bandage according to claim 1, wherein the tacky resin is water-activatable, comprises the reaction product of an isocyanate and polypropylene glycol, and is tacky after water activation.

5. The bandage according to claim 1, wherein the lubricant is in the form of a pellet contained in an interior portion of the core such that upon contact with liquid and application of force to the core, the lubricant is released from the pellet.

6. The bandage according to claim 1, further comprising at least one foam layer having a coating of the lubricant on a surface of the foam layer, the foam layer being within an interior portion of the core such that upon contact with liquid and the application of force to the core, the lubricant is released from the foam.

7. The bandage according to claim 6, wherein the foam layer is folded within the interior portion of the core such that the surface of the foam layer having the lubricant is enclosed within the folded foam layer.

8. The bandage according to claim 6, wherein at least two foam layers are arranged in facing engagement with each other forming a layered foam structure having lubricant within the structure.

9. The bandage according to claim 1, further comprising a liquid-permeable fabric sheet wrapped at least partially around the core, a surface of the sheet facing the core being coated with the lubricant such that upon contact with liquid and the application of force to the core, lubricant is released from the fabric sheet.

10. The bandage according to claim 1, wherein the core is at least partially made from a polymeric composition incorporating the lubricant.

11. The bandage according to claim 10, wherein the polymeric composition comprises a polymer selected from the group consisting of polypropylene, polyethylene and copolymers thereof.

12. The bandage according to claim 1, wherein the lubricant is provided in the form of a powder enclosed within a liquid-permeable fabric casing, the casing being contained in an interior portion of the core such that upon contact with liquid and application of force no the core, the lubricant is released from the casing.

13. A core upon which a casting bandage including a substrate may be wrapped for storage, the core comprising:
   (a) a liquid-permeable base for supporting the substrate; and
   (b) a lubricant associated with the core and adapted to be released from the base, wherein the lubricant renders a surface portion of a substrate to be used as an orthopedic casting bandage substantially non-tacky thereby facilitating the molding, laminating and smoothing of a cast to be formed from the bandage.

14. The core according to claim 13, wherein the base comprises a polymer selected from the group consisting of polypropylene, polyethylene and copolymers thereof.

15. The core according to claim 13, wherein the lubricant is in the form of a pellet contained in an interior portion of the base such that upon contact of the core with liquid and application of force to the core, the lubricant is released from the pellet.

16. The core according to claim 13, further comprising at least one foam layer having a coating of the lubricant on a surface of the foam layer, the foam layer being within an interior portion of the base such that upon contact of the core with liquid and the application of force to the core, the lubricant is released from the foam.

17. The core according to claim 13, wherein the foam layer is folded within the interior portion of the base such that the surface of the foam layer having the lubricant is enclosed within the folded foam layer.

18. The core according to claim 16, wherein at least two foam layers are arranged in facing engagement with each other forming a layered foam structure having lubricant within the structure.

19. The core according to claim 13, further comprising a liquid-permeable fabric sheet wrapped at least partially around the base, a surface of the sheet facing the base being coated with the lubricant such that upon contact of the core with liquid and the application of force to the core, the lubricant is released from the fabric sheet.

20. The core according to claim 13, wherein the base is at least partially made of a polymeric composition incorporating the lubricant.

21. The core according to claim 13, wherein the lubricant is a hydrophilic bisurethane.

22. The core according to claim 13, wherein the lubricant is provided in the form of a powder enclosed within a liquid-permeable fabric casing, the casing being contained in an interior portion of the base such that upon contact of the core with liquid and the application of force to the core, the lubricant is released from the casing.

23. A method for applying an orthopedic cast on a limb, the method comprising the steps of:

(a) providing a tacky orthopedic casting bandage on a core which comprises a lubricant,
 (b) unwinding the bandage from the core;
 (c) applying the bandage to the limb to form a cast;
 (d) applying force to an exterior surface of the core to release the lubricant;
 (e) applying the released lubricant to a tacky surface of the cast; and
 (f) molding, laminating and smoothing a surface portion of the cast which is rendered substantially non-tacky by application of the lubricant.

24. The method of claim 23, further comprising the step of re-applying force to the exterior surface of the core to release the lubricant as needed for further molding, laminating and smoothing of the cast.

25. The method of claim 23, further comprising the step of contacting the core with an activating liquid prior to applying force to the exterior surface of the core when the lubricant is liquid-activatable.

26. The method of claim 23, wherein the force is applied to the exterior surface of the core by rubbing the core between an applier's hands.

27. The method of claim 23, wherein gloved hands are used for releasing the lubricant and for applying the lubricant to the surface portion of the cast.

28. The method of claim 23, wherein the force is applied to the exterior surface of the core by squeezing the core between an applier's hands.

* * * * *